(12) United States Patent
Reschke et al.

(10) Patent No.: US 11,657,044 B2
(45) Date of Patent: May 23, 2023

(54) SEMANTIC PARSING ENGINE

(71) Applicant: PAREXEL International, LLC, Waltham, MA (US)

(72) Inventors: Kevin Reschke, Mountain View, CA (US); Ben Peloquin, San Francisco, CA (US); Christopher Potts, Palo Alto, CA (US); Tharun Paul, Bangalore (IN)

(73) Assignee: PAREXEL International, LLC, Waltham, MA (US)

( * ) Notice: Subject to any disclaimer, the term of this patent is extended or adjusted under 35 U.S.C. 154(b) by 0 days.

(21) Appl. No.: 17/012,319

(22) Filed: Sep. 4, 2020

(65) Prior Publication Data

US 2021/0191924 A1 Jun. 24, 2021

Related U.S. Application Data

(63) Continuation of application No. 15/796,597, filed on Oct. 27, 2017, now abandoned.
(Continued)

(51) Int. Cl.
*G06F 16/242* (2019.01)
*G06F 16/2455* (2019.01)
(Continued)

(52) U.S. Cl.
CPC ........ *G06F 16/243* (2019.01); *G06F 16/2428* (2019.01); *G06F 16/2455* (2019.01);
(Continued)

(58) Field of Classification Search
CPC ................................................ G06F 3/048–05
See application file for complete search history.

(56) References Cited

U.S. PATENT DOCUMENTS 5,450,535 A 9/1995 North
8,423,523 B2 * 4/2013 Vergnory-Mion ........... G06F 16/2456
706/14

(Continued)

FOREIGN PATENT DOCUMENTS

EP 1361522 A2 11/2003

OTHER PUBLICATIONS

Neo4j, "How Graph Search Works", available Jun. 13, 2013, available at <<https://neo4j.com/news/how-graph-search-works/>>, 2 pages (Year: 2013).*

(Continued)

*Primary Examiner* — Daniel Rodriguez
(74) *Attorney, Agent, or Firm* — Wolf, Greenfield & Sacks, P.C.

(57) ABSTRACT

In various example embodiments, a system and methods are presented for converting query structures for information retrieval from graph-based data structures. The systems and methods receive a natural language query including a set of terms and generate an intermediate semantic relationship of the set of terms of the natural language query. The systems and methods generate a graph query including graph terms corresponding to the set of terms of the natural language query defined by a graph database. The systems and methods search one or more datasets associated with the graph database using the graph query and return a set of results based on the graph query.

26 Claims, 9 Drawing Sheets

Related U.S. Application Data

(60) Provisional application No. 62/414,614, filed on Oct. 28, 2016.

(51) Int. Cl.
*G06F 16/901* (2019.01)
*G16H 10/60* (2018.01)
*G06F 40/30* (2020.01)
*G06F 3/0482* (2013.01)

(52) U.S. Cl.
CPC .......... *G06F 16/9024* (2019.01); *G06F 40/30* (2020.01); *G16H 10/60* (2018.01); *G06F 3/0482* (2013.01)

(56) References Cited

U.S. PATENT DOCUMENTS

| | | | |
|---|---|---|---|
| 8,452,851 B2 | 5/2013 | Kabiljo et al. | |
| 8,996,555 B2* | 3/2015 | Kuchmann-Beauger | G06F 16/248 707/763 |
| 9,910,903 B1* | 3/2018 | Jilani | G06F 16/254 |
| 10,191,734 B1* | 1/2019 | Totale | G06F 8/70 |
| 10,262,030 B1* | 4/2019 | Burtenshaw | G06F 16/289 |
| 10,713,252 B1* | 7/2020 | Bourne | G06F 16/9024 |
| 10,878,000 B2* | 12/2020 | Vaquero Gonzalez | G06F 16/25 |
| 11,263,391 B2 | 3/2022 | Potts et al. | |
| 2002/0059069 A1 | 5/2002 | Hsu et al. | |
| 2002/0107844 A1* | 8/2002 | Cha | G06F 16/3344 |
| 2003/0033277 A1 | 2/2003 | Bahulkar et al. | |
| 2003/0069908 A1 | 4/2003 | Anthony et al. | |
| 2003/0149685 A1 | 8/2003 | Trossman et al. | |
| 2003/0212544 A1 | 11/2003 | Acero et al. | |
| 2005/0027664 A1 | 2/2005 | Johnson et al. | |
| 2005/0090911 A1 | 4/2005 | Ingargiola et al. | |
| 2005/0273730 A1 | 12/2005 | Card et al. | |
| 2006/0036564 A1* | 2/2006 | Yan | G06F 16/583 707/E17.02 |
| 2006/0036568 A1 | 2/2006 | Moore et al. | |
| 2006/0047632 A1* | 3/2006 | Zhang | G06F 16/367 |
| 2006/0161521 A1* | 7/2006 | Dettinger | G06F 16/24522 |
| 2006/0242624 A1* | 10/2006 | Mueller-Klingspor | G06F 16/36 717/114 |
| 2006/0248045 A1 | 11/2006 | Toledano et al. | |
| 2007/0106499 A1 | 5/2007 | Dahlgren et al. | |
| 2008/0172407 A1 | 7/2008 | Sacks | |
| 2008/0213768 A1* | 9/2008 | Cai | C12Q 1/6883 435/6.12 |
| 2011/0252355 A1 | 10/2011 | Nixon et al. | |
| 2011/0264291 A1 | 10/2011 | Le Roux et al. | |
| 2011/0295788 A1* | 12/2011 | Kowalski | G06F 16/90332 706/50 |
| 2012/0072468 A1 | 3/2012 | Anthony et al. | |
| 2012/0221558 A1* | 8/2012 | Byrne | G06Q 10/06 707/723 |
| 2012/0246153 A1* | 9/2012 | Pehle | G06F 16/3322 707/723 |
| 2012/0259895 A1* | 10/2012 | Neely, III | G06F 16/367 707/E17.011 |
| 2013/0151572 A1 | 6/2013 | Brocato et al. | |
| 2013/0262449 A1 | 10/2013 | Arroyo et al. | |
| 2013/0262501 A1* | 10/2013 | Kuchmann-Beauger | G06F 16/24535 707/769 |
| 2013/0332438 A1* | 12/2013 | Li | G06F 16/24575 707/706 |
| 2014/0059084 A1 | 2/2014 | Adams et al. | |
| 2014/0098101 A1 | 4/2014 | Friedlander et al. | |
| 2014/0136520 A1* | 5/2014 | Digana | G06F 16/245 707/722 |
| 2014/0214834 A1* | 7/2014 | Ozonat | G06F 16/9024 707/748 |
| 2014/0222826 A1* | 8/2014 | DaCosta | G06F 16/2228 707/741 |
| 2014/0236579 A1* | 8/2014 | Kurz | G06F 40/284 704/9 |
| 2014/0244325 A1 | 8/2014 | Cartwright | |
| 2014/0258301 A1 | 9/2014 | Misra et al. | |
| 2014/0337306 A1 | 11/2014 | Gramatica | |
| 2015/0095303 A1* | 4/2015 | Sonmez | G06N 5/003 707/707 |
| 2015/0117216 A1 | 4/2015 | Anand et al. | |
| 2015/0127677 A1* | 5/2015 | Wang | G06F 16/9024 707/769 |
| 2015/0161521 A1* | 6/2015 | Shah | G06F 3/0481 715/705 |
| 2015/0324425 A1* | 11/2015 | Behzadi | G06F 16/9537 707/759 |
| 2015/0350440 A1* | 12/2015 | Steiner | H04M 3/5232 379/266.01 |
| 2015/0370787 A1* | 12/2015 | Akbacak | G06F 40/47 704/2 |
| 2016/0117322 A1* | 4/2016 | Ramaswamy | G06F 16/951 707/756 |
| 2016/0117752 A1* | 4/2016 | Chacko | G06Q 30/0631 705/26.7 |
| 2016/0162456 A1 | 6/2016 | Munro et al. | |
| 2016/0162458 A1 | 6/2016 | Munro et al. | |
| 2016/0179877 A1* | 6/2016 | Koerner | G06F 16/90324 707/721 |
| 2016/0267128 A1* | 9/2016 | Dumoulin | G06F 16/3329 |
| 2016/0275196 A1* | 9/2016 | Lee | G06F 16/24522 |
| 2016/0311113 A1* | 10/2016 | Markey | B25J 13/02 |
| 2017/0249309 A1* | 8/2017 | Sarikaya | G06F 16/24565 |
| 2017/0270418 A1 | 9/2017 | Reschke et al. | |
| 2017/0277841 A1 | 9/2017 | Shankar et al. | |
| 2017/0308620 A1* | 10/2017 | Cao | G06F 16/13 |
| 2018/0075359 A1 | 3/2018 | Brennan et al. | |
| 2018/0081937 A1* | 3/2018 | Broecheler | G06F 16/2322 |
| 2018/0121500 A1 | 5/2018 | Rescchke et al. | |
| 2018/0121546 A1 | 5/2018 | Dingwall et al. | |
| 2019/0034591 A1 | 1/2019 | Mossin et al. | |
| 2020/0293712 A1 | 9/2020 | Potts et al. | |
| 2022/0129766 A1 | 4/2022 | Potts et al. | |
| 2022/0253594 A1 | 8/2022 | Potts et al. | |

OTHER PUBLICATIONS

International Search Report and Written Opinion dated Jan. 17, 2018 in connection with International Application No. PCT/US2017/058864.

International Preliminary Report on Patentability dated Apr. 30, 2019 in connection with International Application No. PCT/US2017/058864.

International Search Report and Written Opinion dated May 5, 2020 in connection with International Application No. PCT/US2019/068416.

Invitation to Pay Additional Fees for International Application No. PCT/US2019/068416 dated Feb. 24, 2020.

International Search Report and Written Opinion dated Jun. 15, 2020 in connection with International Application No. PCT/US2020/022107.

International Search Report and Written Opinion dated Feb. 2, 2018 in connection with International Application No. PCT/US2017/058859.

International Search Report and Written Opinion dated May 26, 2017 in connection with International Application No. PCT/US2017/022483.

Extended European Search Report dated Aug. 12, 2022 in connection with European Application No. 19902557.8.

Extended European Search Report dated Nov. 9, 2022 in connection with European Application No. 20770117.8.

International Preliminary Report on Patentability dated Sep. 23, 2021 in connection with International Application No. PCT/US2020/022107.

(56) References Cited

OTHER PUBLICATIONS

[No Author Listed], Data modeling. Wikipedia. Oct. 2018. 8 pages. URL:https://en.wikipedia.org/wiki/data_modeling [last accessed Dec. 14, 2018].
[No Author Listed], Transform Complex Text Documents into Data, Insights, & Value. 2022, 12 pages. URL:https://www.lexalytics.com [last accessed Aug. 15, 2022].
Fellbaum [ed], WordNet: An Electronic Lexical Database. 1998, 6 pages. MIT Press.
Forest et al., Dedupe. 2022, 5 pages. URL:https://github.com/datamade/dedupe. [last accessed Apr. 7, 2022].
Gawriljuk et al., A scalable approach to incrementally building knowledge graphs. International conference on theory and practice of digital libraries. Sep. 2016, pp. 188-199.
Kaufmann et al., Evaluating the usability of natural language query languages and interfaces to Semantic Web knowledge bases. Journal of Web Semantics. Nov. 2010;8(4):377-93. DOI:10.1016/j.websem.2010.06.001.
Li et al., Under the hood: The natural language interface of Graph Search. Apr. 29, 2013. 9 pages. URL:https://code.facebook.com/posts/316353631844205/under-the-hood-the-natural-language-interface-of-graph-search [last accessed Apr. 7, 2022].
Park et al., Introducing: Project open data. May 16, 2013. 3 pages. URL:https://www.whitehouse.gov/blog/2013/05/16/introducing-project-open-data [last accessed Apr. 7, 2022].
Reddy et al., Large-scale semantic parsing without question-answer pairs. Transactions of the Association for Computational Linguistics. Dec. 1, 2014;2:377-92.
Rui et al., Visualization and Forecast Analysis of Science and Technology Intelligence Based on Knowledge Graph. 2018 17th International Symposium on Distributed Computing and Applications for Business Engineering and Science (DCABES). Oct. 2018, pp. 44-47.
Setia, Create a knowledge base using domain specific documents and the mammoth python library. Jun. 17, 2018. 6 pages. URL:http://web.archive.org/web/20180617181315/https://github.com/IBM/build-knowledge-base-with-domain-specific-documents [last accessed Jul. 27, 2022].
Stichbury, WTF is a knowledge graph? Hacker Noon. May 10, 2017. 10 pages. URL:https://hackernoon.com/wtf-is-a-knowledge-graph-a16603a1a25f [last accessed Nov. 17, 2018].
Sun et al., Data Processing and Text Mining Technologies on Electronic Medical Records: A Review. Hindawi. Journal of Healthcare Engineering. Apr. 2018. 10 pages. URL:https://www.hindawi.com/journals/jhe/2018/4302425 [last accessed Aug. 15, 2022].
Yankova, Text Mining & Graph Databases—Two Technologies that Work Well Together. Jul. 5, 2014. 7 pages. URL:https://www.ontotext.com/blog/text-mining-graph-databases-work-well-together [last accessed Aug. 15, 2022].
Zettlemoyer et al., Online learning of relaxed CCG grammars for parsing to logical form. Proceedings of the 2007 Joint Conference on Empirical Methods in Natural Language Processing and Computational Natural Language Learning (EMNLP-CoNLL). Jun. 2007, pp. 678-687.

\* cited by examiner

SEMANTIC PARSING ENGINE

CLAIM FOR PRIORITY

This application is a continuation application of U.S. application Ser. No. 15/796,597, filed Oct. 27, 2017, which claims the benefit of priority to U.S. Provisional Application No. 62/414,614, filed Oct. 28, 2016, which is hereby incorporated by reference in its entirety.

TECHNICAL FIELD

The subject matter disclosed herein generally relates to the technical field of special-purpose machines for dataset clustering and search engines that facilitate data set navigation and database queries, including software-configured computerized variants of such special-purpose machines and improvements to such variants, and to the technologies by which such special-purpose machines become improved compared to other special-purpose machines that facilitate generation of search results and relational links between discrete data sets using a canonical semantic layer.

BACKGROUND

Conventionally, data systems organize data into discrete sets and using standardized identifiers, categories, and characteristics. This organization enables easier and faster searching by organizing data published or consolidated by a single entity. Data systems searching differing data sets, published across multiple entities, encounter difficulties in correlating organizational structures. Further difficulties are encountered where data sets are provided in differing formats. While conventional data systems may be able to retrieve distinct documents or elements from multiple data sets, these data systems often provide the documents with no context or relation to other documents presented within the same or similar search results. As a result, conventional data systems attempting to draw inferences or determine links between data sets often present results with unacceptable degrees of uncertainty.

BRIEF DESCRIPTION OF THE DRAWINGS

Various ones of the appended drawings merely illustrate example embodiments of the present disclosure and cannot be considered as limiting its scope.

Figure 1:
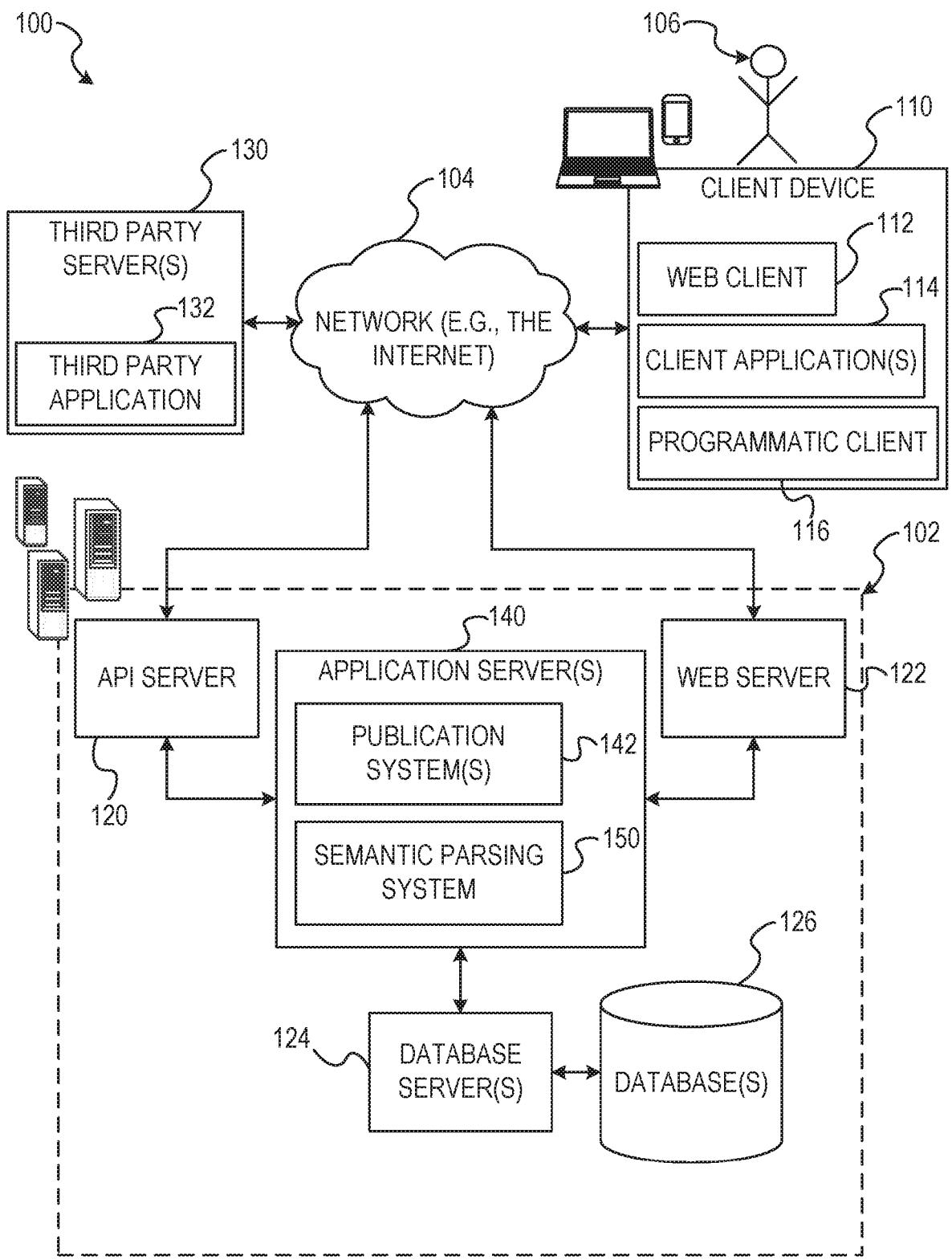
FIG. 1 is a block diagram illustrating a networked system, according to some example embodiments.

The headings provided herein are merely for convenience and do not necessarily affect the scope or meaning of the terms used.

DETAILED DESCRIPTION

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

Systems and method described herein define a semantic parsing system or semantic parsing engine for dataset graphs method for large scale knowledge graphs (e.g., health knowledge graphs) that is graph-backed in the sense that its grammar and semantic concepts are derived automatically from the graph schema. The methods and systems also enable a superior search experience compared to raw database queries. Although described with respect to healthcare information, technologies, data sets, and semantic relationships, it should be understood that the systems and methods described herein are able to generate a connected knowledge graph by unifying any suitable data set, information, set of publications, or set of documents using semantic layers organizing or underlying the data sources and using machine learning techniques to generate models to incorporate new edges and relationships into the canonical layer.

An enormous amount of datasets (e.g., such as public health released by governments like the United States, industries, or individual entities) have been made available for public use over the last few years. Taken together, these datasets have the potential to provide a comprehensive picture of the various industry domains. In the example of the healthcare domain: drugs, procedures, diseases, providers, and so forth. Only patient-level data is missing, because of privacy considerations, but census and survey data still support analyses based on fine-grained demographics. These releases outline not only the core ontology of the healthcare space (e.g., doctors, hospitals, manufacturers, drugs, devices, procedures, and so on), but also support serious inquiry into the dynamics of the space, including prescribing behaviors for providers, recalls and adverse events, hospital quality evaluations, population-level psychological and social characteristics, and so forth. Where released datasets involve other industries, similar ontological outlines may be modeled and dynamics of industry practice, governmental regulation, and users (e.g., customer, practitioner, or third-party entities) may be similarly investigated and modeled. Further, modeling of industry dynamics and ontologies supports or enables drawing of inferences and links using modeled representations of the datasets.

The systems and methods disclosed herein present an approach to developing semantic parsers over large knowledge graphs, such as large health knowledge graphs (HKGs) derived from these public datasets. These semantic parsers are graph-backed, such that the schema for the target graph is used to define the core space of entities, concepts, and relations; it provides the initial seed sets for defining the semantic lexicon; and it helps delimit the space of rules for syntactic and semantic combination. Thus, very large and complex grammars are easily instantiated, addressing one of the major bottlenecks for semantic parsing at scale.

The result of the systems and methods disclosed herein is expanded access to public health information, so the semantic parser, in some example embodiments, is natural language search into health knowledge graphs. Natural language searching may differ from a database query language, which can be cumbersome even for experts and which puts most information out of reach for regular users. The promise of natural language search is that it removes these obstacles. To assess progress on this accessibility issue, the present disclosure includes a usability study comparing the semantic parsing system with issuing raw graph query language statements. All participants were experts in the graph query language. As a group, they completed tasks faster and in fewer attempts with our system than with raw queries, and they preferred our system for everything except very complex queries.

With reference to FIG. 1, an example embodiment of a high-level client-server-based network architecture 100 is shown. A networked system 102, in the example forms of a network-based predictive modeling system, provides server-side functionality via a network 104 (e.g., the Internet or wide area network (WAN)) to one or more client devices 110. FIG. 1 illustrates, for example, a web client 112 (e.g., a browser, such as the INTERNET EXPLORER® browser developed by Microsoft® Corporation of Redmond, Wash. State), an application 114, and a programmatic client 116 executing on client device 110.

The client device 110 may comprise, but is not limited to, mobile phones, desktop computers, laptops, personal digital assistants (PDAs), smart phones, tablets, ultra books, netbooks, laptops, multi-processor systems, microprocessor-based or programmable consumer electronics, game consoles, set-top boxes, or any other communication device that a user may utilize to access the networked system 102. In some embodiments, the client device 110 may comprise a display component (not shown) to display information (e.g., in the form of user interfaces). In further embodiments, the client device 110 may comprise one or more of a touch screens, accelerometers, gyroscopes, cameras, microphones, global positioning system (GPS) devices, and so forth.

The client device 110 may be a device of a user that is used to perform a transaction involving object data and predictive models within the networked system 102. One or more users 106 may be a person, a machine, or other means of interacting with client device 110. In embodiments, the user 106 is not part of the network architecture 100, but may interact with the network architecture 100 via client device 110 or another means. For example, one or more portions of network 104 may be an ad hoc network, an intranet, an extranet, a virtual private network (VPN), a local area network (LAN), a wireless LAN (WLAN), a WAN, a wireless WAN (WWAN), a metropolitan area network (MAN), a portion of the Internet, a portion of the Public Switched Telephone Network (PSTN), a cellular telephone network, a wireless network, a WiFi network, a WiMax network, another type of network, or a combination of two or more such networks. Each of the client device 110 may include one or more applications (also referred to as "apps") such as, but not limited to, a web browser, messaging application, electronic mail (email) application, and the like.

One or more users 106 may be a person, a machine, or other means of interacting with the client device 110. In example embodiments, the user 106 is not part of the network architecture 100, but may interact with the network architecture 100 via the client device 110 or other means. For instance, the user provides input (e.g., touch screen input or alphanumeric input) to the client device 110 and the input is communicated to the networked system 102 via the network 104. In this instance, the networked system 102, in response to receiving the input from the user, communicates information to the client device 110 via the network 104 to be presented to the user. In this way, the user can interact with the networked system 102 using the client device 110.

An application program interface (API) server 120 and a web server 122 are coupled to, and provide programmatic and web interfaces respectively to, one or more application servers 140. The application servers 140 may host one or more publication systems 142 and a semantic parsing systems 150, each of which may comprise one or more components or applications and each of which may be embodied as hardware, software, firmware, or any combination thereof. The application servers 140 are, in turn, shown to be coupled to one or more database servers 124 that facilitate access to one or more information storage repositories or database(s) 126. In an example embodiment, the databases 126 are storage devices that store information to be posted (e.g., publications or listings) to the publication system 142. The databases 126 may also store object data, historical data, and predictive modeling data in accordance with example embodiments.

Additionally, a third-party application 132, executing on third party server(s) 130, is shown as having programmatic access to the networked system 102 via the programmatic interface provided by the API server 120. For example, the third-party application 132, utilizing information retrieved from the networked system 102, supports one or more features or functions on a website hosted by the third party.

The publication system 142 may provide a number of publication, archival, and data storage functions and services to users 106 that access the networked system 102. For example, the publication system 142 may gather, publish, and store object data, historical data for one or more objects, sales data for one or more objects, revenue data for one or more objects, release data for one or more objects, competitor data for one or more objects, publicly distributed datasets for industries, datasets for users or practitioners associated with identified industries, census and other demographic data informing industry datasets, and taxonomy data sets comprising ontological descriptions of industry datasets. The publication system 142 may publish the received or accessed datasets or may provide a consolidated database of the received or accessed datasets to an internal database or publicly available database to enable generation of predictive models and dataset network models based on the datasets. In some embodiments, the publication system 142 accesses one or more third party servers or databases (e.g., the third-party server 130) to retrieve, modify, and provision the object data within the database 126.

The semantic parsing systems 150 may provide functionality operable to perform various dataset network model generation and predictive model generation and manipulation functions, as well as functions for generating graphical representations of datasets, dataset network models, and predictive models. For example, the semantic parsing systems 150 accesses datasets from the databases 126, the third-party servers 130, the publication system 142, the client device 110, and other sources. In some example embodiments, the semantic parsing systems 150 analyzes portions of the sets of object data to generate dataset network models and predictive models interpreting, drawing inferences from, and supplying search and result retrieval functionality for the accessed datasets. In some example embodiments, the semantic parsing systems 150 communicates with the publication systems 142 to access the datasets and transmit queries received by the semantic parsing systems 150 to the publication system 142. In an alternative embodiment, the semantic parsing systems 150 may be a part of the publication system 142.

Further, while the client-server-based network architecture 100 shown in FIG. 1 employs a client-server architecture, the present inventive subject matter is of course not limited to such an architecture, and could equally well find application in a distributed, or peer-to-peer, architecture system, for example. The various publication system 142 and semantic parsing systems 150 could also be implemented as standalone software programs, which do not necessarily have networking capabilities.

The web client 112 may access the various publication and dataset network modeling systems 142 and 150 via the web interface supported by the web server 122. Similarly, the programmatic client 116 accesses the various services and functions provided by the publication and dataset network modeling systems 142 and 150 via the programmatic interface provided by the API server 120.

Additionally, a third-party application(s) 128, executing on a third-party server(s) 130, is shown as having programmatic access to the networked system 102 via the programmatic interface provided by the API server 114. For example, the third-party application 128, utilizing information retrieved from the networked system 102, may support one or more features or functions on a website hosted by the third party. The third-party website may, for example, provide one or more promotional, marketplace, data repository, company interaction, or object tracking functions that are supported by the relevant applications of the networked system 102.

Figure 2:
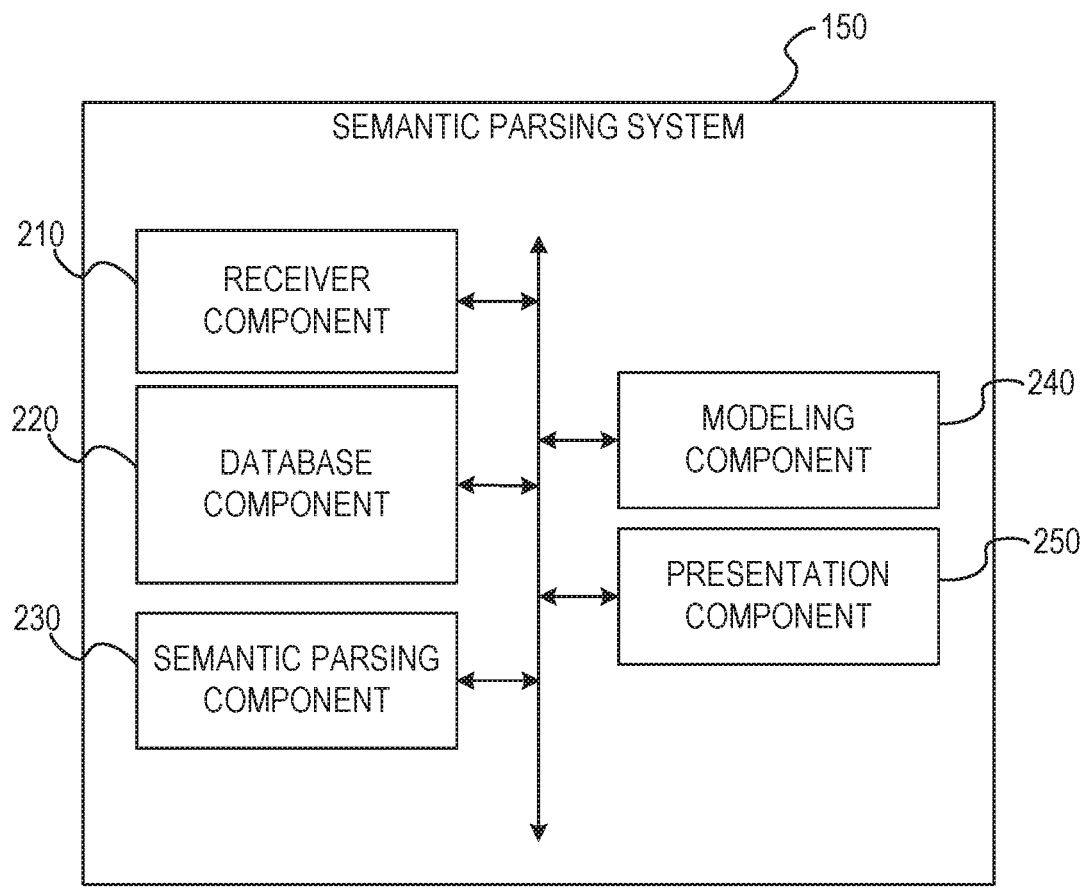
FIG. 2 is a block diagram of an example semantic parsing system, according to various embodiments.

FIG. 2 is a block diagram illustrating components of the semantic parsing systems 150, according to some example embodiments. The semantic parsing systems 150 is shown as including a receiver component 210, a database component 220, a semantic parsing component 230, a modeling component 240, and a presentation component 250 all configured to communicate with one another (e.g., via a bus, shared memory, or a switch). Any one or more of the components described herein may be implemented using hardware (e.g., one or more processors of a machine) or a combination of hardware and software. For example, any component described herein may configure a processor (e.g., among one or more processors of a machine) to perform operations for which that component is designed. Moreover, any two or more of these components may be combined into a single component, and the functions described herein for a single component may be subdivided among multiple components. Furthermore, according to various example embodiments, components described herein as being implemented within a single machine, database(s) 126, or device (e.g., client device 110) may be distributed across multiple machines, database(s) 126, or devices.

Figure 3:
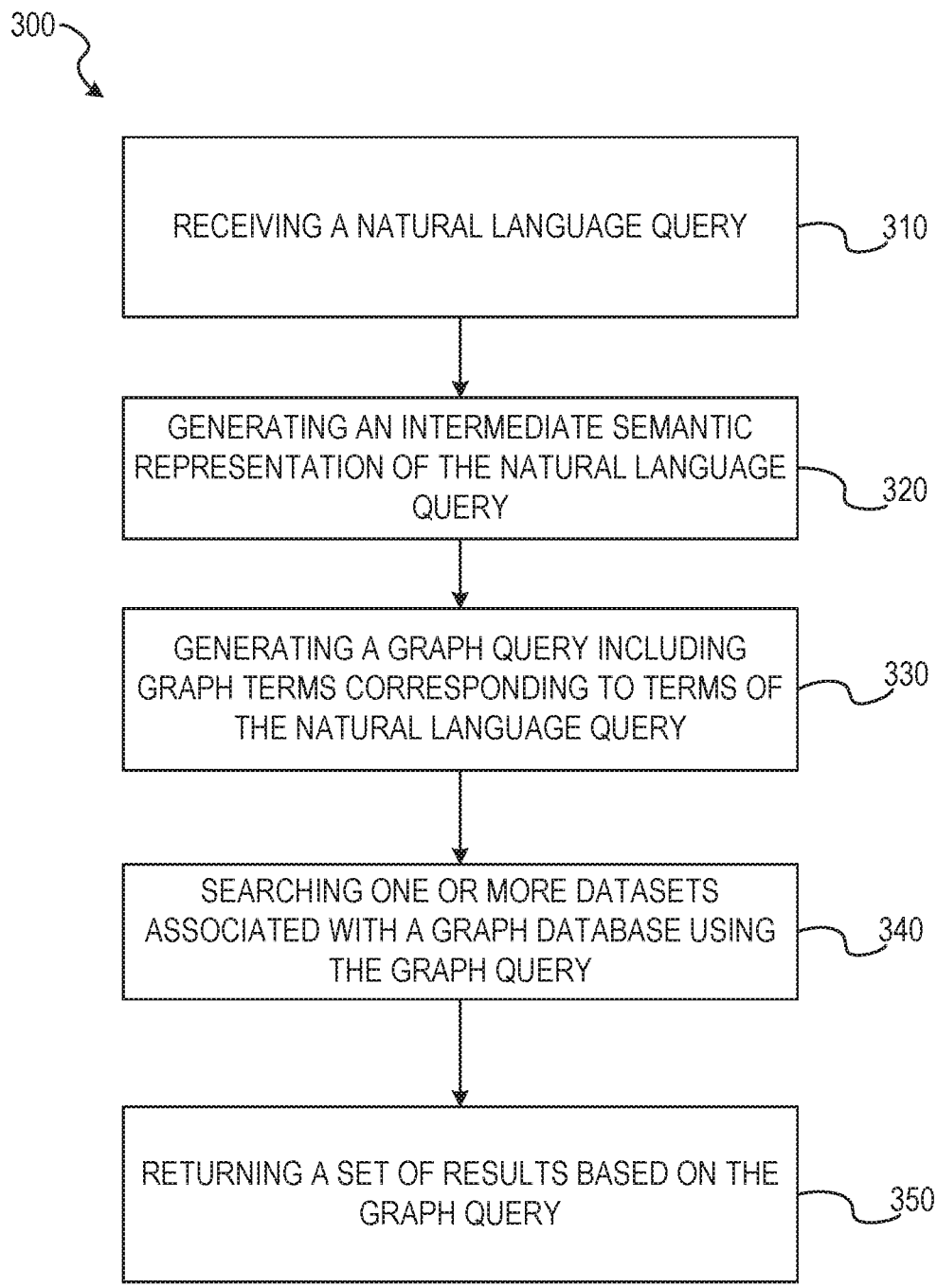
FIG. 3 is a flowchart illustrating an example method of converting query structures for information retrieval from graph-based data structures using the semantic parsing system, according to various embodiments.

In FIG. 3, is a flowchart of operations of the semantic parsing system 150 in performing a method 300 of converting query structures for information retrieval from graph-based data structures using a semantic parsing system, according to some example embodiments. Operations of the method 300 may be performed by the semantic parsing system 150, using components described herein.

Figure 4:
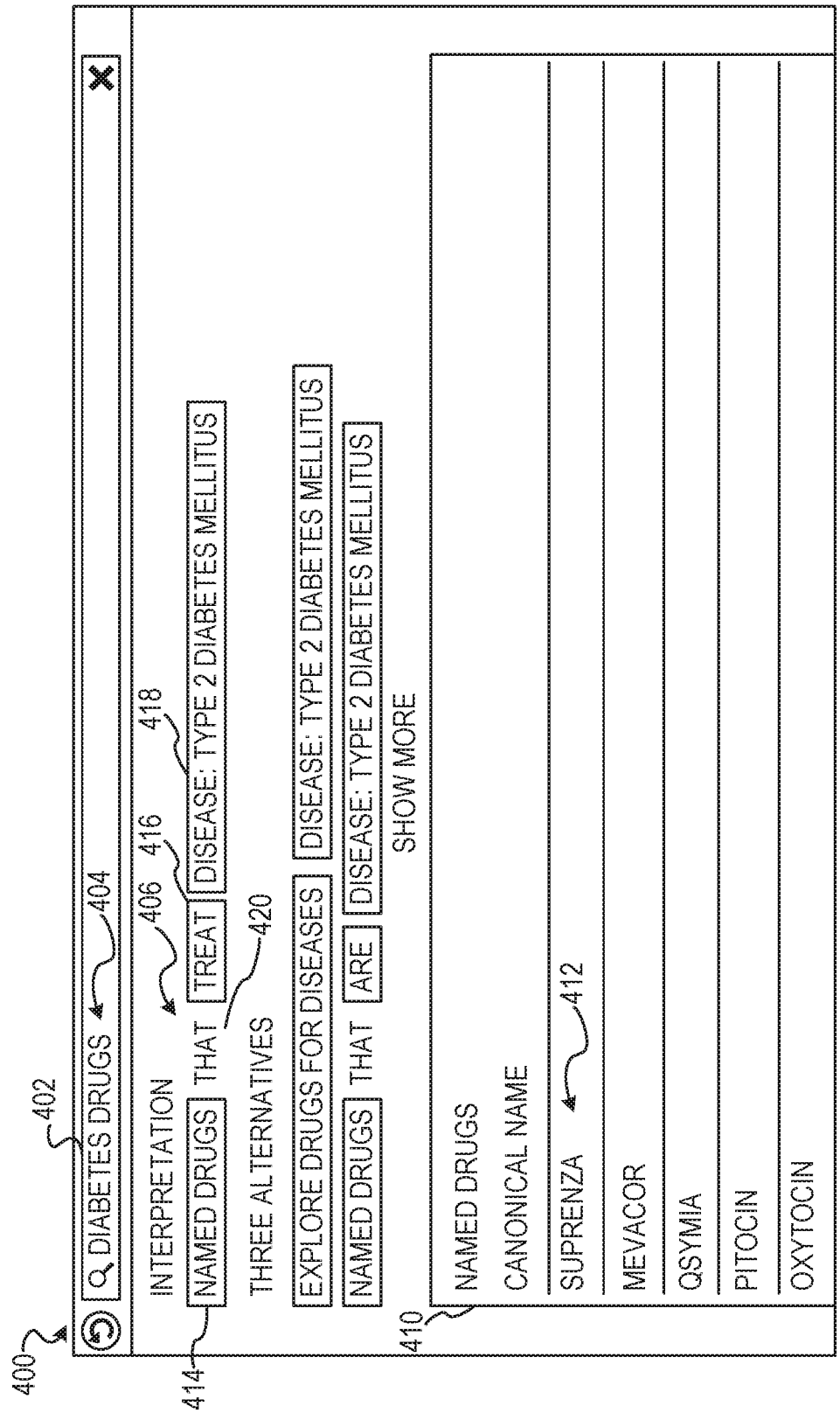
FIG. 4 is an example graphical user interface of the semantic parsing system, according to various embodiments.

In operation 310, the receiver component 210 receives a natural language query. The natural language query may comprise a set of terms. The natural language query may be transmitted to the semantic parsing system 150 to perform a search on one or more databases or datasets connected together in a knowledge graph. The natural language query may include terms generated by a user associated with the query, such as by text entry. As shown in FIG. 4, the user may initially be presented with a text entry field 402 within a graphical user interface 400. The text entry field 402 may be configured to receive data entered by a user. The natural language query 404 may be displayed within the text entry field 402 upon entry by the user.

The knowledge graph may be comprised of a plurality of subgraphs connected together. The subgraphs may initially be isolated from one another, but connected by forming edges extending between related nodes of the isolated subgraphs in order to generate the knowledge graph. For example, the knowledge graph may be formed from public health datasets. The public health datasets under consideration may not be released by a single entity using a consistent set of identifiers. Rather, each dataset presents a partial, potentially biased view of the world, the union of all the information in them is likely to be inconsistent, and establishing even simple links between entities often must be cast as a model-based inference under uncertainty.

In some embodiments, the knowledge graph is formed from the distinct datasets in a manner producing a single connected graph with high confidence. For example, public datasets may be assembled into a connected graph, united thematically around common or related subjects, entities, or information. An example of suitable public datasets may include datasets related to physicians and prescribing behavior. Example public datasets may include, but are not limited to, National Provider Identifier, a registry of healthcare providers; CMS Physician Compare, data on physicians and their practices; CMS Open Payments Research, research support by manufacturers; Healthcare Taxonomy, three-level classification of medical specialties; CMS Prescriptions, information on prescriptions written under Medicare Part D; and FDA Drug Labels, information relating to drugs and their associated and regulated metadata. As described in more detail below, the natural language queries, seeking to surface information from the knowledge graph, may be formulated to take advantage of the structure of the knowledge graph.

Nodes and edges within the knowledge graph may be associated with types. Each type of node or edge may be associated with numerous attributes. For example, some edges may represent identity-relation edges and may be added based on identifiers, heuristic methods, and model-based inferences, with the direction chosen arbitrarily. NPI identities connect NPI, CMS Physician Compare, and CMS Prescriptions via providers. Taxonomy codes connect the NPI with the Healthcare Taxonomy. Brand and generic names connect CMS Prescriptions to FDA Drug Labels via drugs. The CMS Open Payments Research dataset, unlike CMS Prescriptions, may not contain NPI identifications, so the knowledge graph or models used to traverse the knowledge graph may be trained using a log-linear classifier and using a Dedupe package. Such training methodology may match nodes or attributes, characteristics, or metadata for nodes with high confidence. The resulting graph may be instantiated in Neo4j. In some instances, the knowledge graph may comprise a plurality of nodes and edges, each numbering in the millions.

In operation 320, the semantic parsing component 230 generates an intermediate semantic representation of the set of terms of the natural language query. The intermediate semantic representation may be a logical form representation. The semantic parsing component 230 may automatically convert the natural language query to the logical form representation upon receipt of the natural language query from the text entry field 402 of the graphical user interface 400 depicted in FIG. 4. In some instances, the semantic parsing component 230 includes PYTHON® code implemented at a webserver serving the graphical user interface 400 to a computing device of a user. The semantic parsing component 230 may be an in-memory parser. In some embodiments, the semantic parsing component 230 and the modeling component 240 form a single component handling translation of the natural language query to a graph query, described below.

In some embodiments, the semantic parsing component 230 comprises a graph-backed semantic parser. The semantic parsing component 230 may configure, modify, or translate the natural language query through one or more operations to navigate around the challenges of distinct datasets incorporated into a single knowledge graph and resulting from inconsistencies among the distinct datasets. The knowledge graph may be determined by the structure of the underlying databases. The edges connecting discrete sub-graphs may be added to connect these isolated subgraphs based on related attributes of individual nodes within the connected subgraphs.

In some embodiments, the intermediate semantic representation is generated using one or more operations or sub-operations. For example, the semantic parsing component 230 may parse the set of terms of the natural language query to identify types of terms included in the natural language query. The semantic parsing component 230 may identify types such as entities, actions, comparisons, nouns, verbs, adjectives, adverbs, and other suitable types. The semantic parsing component 230 may then identify one or more relationships between the set of terms. The relationships may be based on proximity of the terms, syntactic or grammatical interactions of the terms, nature of the terms (e.g., comparative, superlative, etc.), intersecting relationships or terms, sorting relationships or terms, and any other suitable relationship. Once the natural language query has been parsed, the semantic parsing component 230 converts the set of terms to a logical form representation based on the one or more relationships. In some embodiments, the logical form representation is the intermediate semantic representation of the natural language query.

In some embodiments, a grammar aspect of graph-backing, in the semantic parsing component 230, is employed in translating the natural language query into the intermediate semantic representation. In previous systems, creating and maintaining grammar, syntax, and semantic grammars was a large undertaking, done separately for each queried database. The semantic parsing component 230 may employ a graph schema of the knowledge graph to define at least a portion of the grammar rules of the semantic parsing component 230. For example, where the schema contains Person→WORKS_IN→Location, the semantic parsing component 230 may create a syntax rule, such as "PERSON ! LOCATION PERSON" and a semantic rule, such as "T (works_in ({0}; {1})." Since relations that are intuitively direct may correspond to long paths in the graph, the semantic parsing component 230 may additionally allow bridging concept terms in the logical forms that have no syntactic realization but establish the desired semantic links, equivalently, graph paths.

For example, where a natural language query includes terms of "top JANUVIA® prescribers in New York," the query involves three uses of an intersect operator as well as one use of a sorted operator. The sorted operator may be triggered by the superlative modifier "top." Where the semantic parsing component 230 is transforming the natural language query for the healthcare knowledge graph described above, the semantic parsing component 230 may use one or more semantic or syntax rules associated with the CMS Prescriptions sub-graph, where that sub-graph uses internal 'cms_drug' nodes. Further, a bridging concept may be triggered to relate a provider to a drug based on expectations generated by relationships of nodes within the knowledge graph.

In operation 330, the modeling component 240 generates a graph query including graph terms corresponding to the set of terms of the natural language query. As shown in FIG. 4, the graph query may be represented within the graphical user interface 400 as a set of selectable user interface elements 406. In some embodiments, generation of the graph query is based on the intermediate semantic representation. The graph terms may be defined based on a graph-based database and the set of terms of the natural language query. In some embodiments, the graph query may comprise or be generated as a cypher query. The modeling component 240 may map one or more of the natural language query and the intermediate semantic representation into a declarative query language cypher, such as an Neo4j query language Cypher. In some embodiments, the modeling component 240 interacts with the semantic parsing component 230, receiving the intermediate semantic representation and converting the representation into the graph query. The modeling component 240 may be an in-memory language model.

In some embodiments, the modeling component 240 uses a language model, an entity index, a lexical resource, and grammar or syntax rules associated with the knowledge graph to transform the natural language query or the intermediate semantic representation into the graph query with the graph terms. In such instances, the modeling component 240 and the resulting graph query may be defined by the underlying knowledge graph. For example, the language models used for entity detection may be trained on name-type attributes of nodes. The language models, incorporated in the modeling component 240, may resolve those entities using graph-backed operations. For example, an "Entity index" may be automatically created from a database or the knowledge graph and provide fast look-up for the semantic parsing component 230 or the modeling component 240. A "Lexical analysis" operation may be similarly graph-backed, incorporating node and edge type-names to provide the core lexicon. The core lexicon may then be expand using additional databases or data sets, such as third-party data sets like Wiktionary, WordNet, and heuristic morphological expansions.

In operation 340, the database component 220 searches one or more datasets associated with the graph database using the graph query. The modeling component 240 may pass the graph query to the database component 220 for searching against the datasets included in the knowledge graph. In some embodiments, the database component 220 includes a search engine to perform an entity search or other term based searches using the graph query. In some embodiments, the database component 220 parses or otherwise searches attributes, characteristics, and other information of nodes, clusters, datasets, and subgraphs of the knowledge graph to identify nodes, entities, links, databases, datasets, or records, relating to one or more elements of the graph query. The elements of the graph query may be individual elements, search terms, features, or other query elements representative of the natural language query.

In operation 350, the presentation component 250 returns a set of results based on the graph query. The presentation component 250 may return the set of results in the graphical user interface 400 of FIG. 4. In some embodiments, as shown in FIG. 4, the set of results are presented in a result area 410. The result area 410 may be populated with a set of selectable interface icons 412. Each selectable interface icon may correspond to a link, dataset, node, entity or record of the knowledge graph. Selection of a selectable interface icon may direct the graphical user interface 400 to a pertinent record location associated with a specified result.

Figure 5:
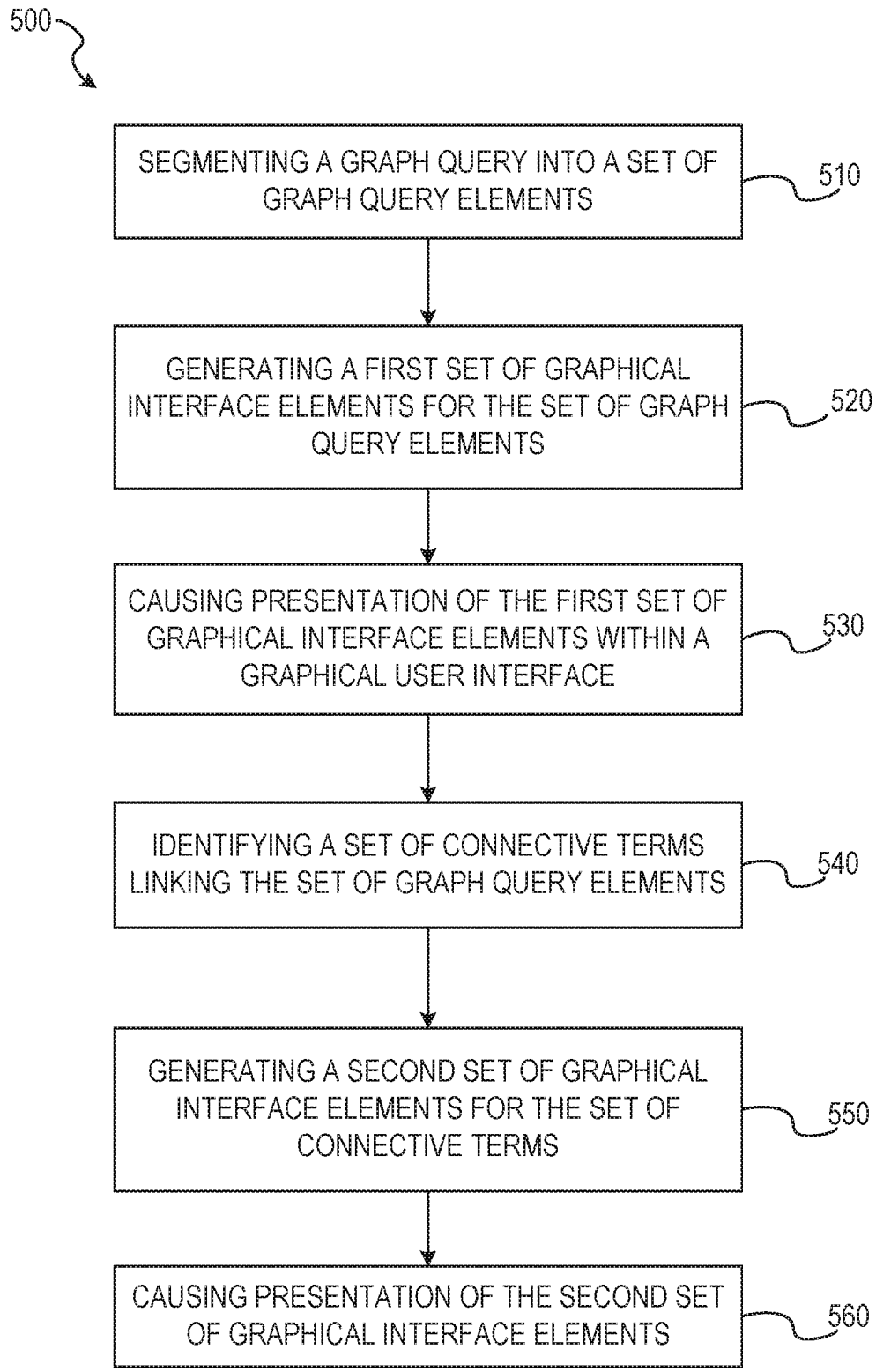
FIG. 5 is a flowchart illustrating an example method of converting query structures for information retrieval from graph-based data structures using the semantic parsing system, according to various embodiments.

In FIG. 5, is a flowchart of operations of the semantic parsing system 150 in performing a method 500 of converting query structures for information retrieval from graph-based data structures, according to some example embodiments. Operations of the method 500 may be performed by the semantic parsing system 150, using components described herein.

In operation 510, the modeling component 240 segments a graph query into a set of graph query elements. As shown in FIG. 4, the graph query may be segmented into the set of graph query elements, such that each graph query element corresponds to a selectable user interface element of the set of selectable user interface elements 406. In some embodiments, each graph query element may represent a portion of the natural language query 404 or an interpretation of at least a portion of the natural language query 404, such as a term, entity, or relationship within the natural language query 404.

In operation 520, the presentation component 250 generates a first set of graphical interface elements 414, 416, and 418 corresponding to the set of graph query elements. The first set of graphical interface elements 414, 416, and 418 may be selected as graph query elements which are stated or inferred from the natural language query 404.

In operation 530, the presentation component 250 causes presentation of the first set of graphical interface elements within a graphical user interface. The first set of graphical interface elements may be contemporaneously presented with the set of terms of the natural language query. As shown in FIG. 4, once generated, the first set of graphical interface elements 414, 416, and 418 may be presented within the graphical user interface 400.

In operation 540, the modeling component 240 identifies a set of connective terms linking the set of graph query elements as an approximation of the natural language query. As shown in FIG. 4, the set of connective terms may be inferred from the natural language query 404 without being explicitly stated or included within the natural language query. The modeling component 240 may cooperate with the semantic parsing component 230 to identify relationships between words in the natural language query 404 that indicate, suggest, or imply the connective term or set of connective terms.

In operation 550, the presentation component 250 generates a second set of graphical interface elements. As shown in FIG. 4, the second set of graphical interface elements 420 may be generated as selectable or non-selectable user interface elements. The second set of graphical interface elements may correspond to the set of connective terms. In some embodiments, as shown in FIG. 4, the second set of graphical interface elements 420 may be generated with respect to the first set of graphical interface elements 414, 416, and 418. In such embodiments, the second set of graphical interface elements 420, representing connective terms, may be generated to fill in areas between the first set of graphical interface elements 414, 416, and 418 to generate a user readable representation of the graph query.

In operation 560, the presentation component 250 causes presentation of the second set of graphical interface elements. The second set of graphical interface elements 420 may be presented contemporaneously with the first set of graphical interface elements 414, 416, and 418, and the set of terms of the natural language query 404. In some embodiments, the second set of graphical interface elements are distributed among the set of graph query elements depicted within the first set of graphical interface elements.

In some embodiments, alternative interpretations or search terms may be presented within the graphical user interface 400 of FIG. 4. In such embodiments, during operations 320-330, the semantic parsing system 150 may identify alternative search terms based on one or more of the set of terms of the natural language query. In some embodiments, the alternative search terms may be generated based on one or more of the natural language query, the intermediate semantic representation, and the graph query generated in method 300. The presentation component 250 may generate a set of alternative interface elements corresponding to the set of alternative search terms to populate a portion of the graphical user interface 400. Once generated, the presentation component 250 may cause presentation of the set of alternative interface elements and alternative search terms. The alternative interface elements and search terms may be presented contemporaneously with interface elements corresponding to the graph query element, the graph query, and the natural language query.

Figure 6:
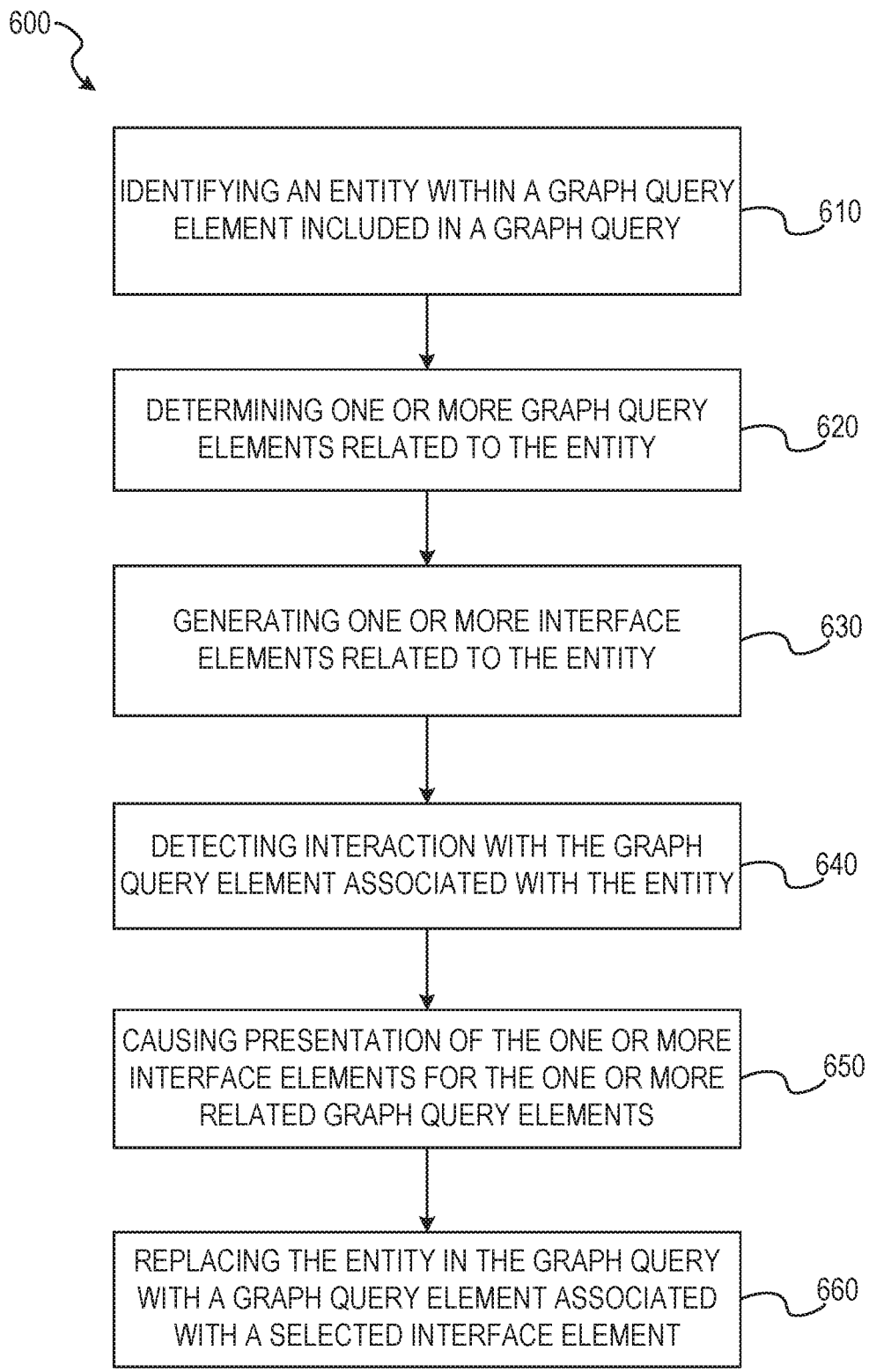
FIG. 6 is a flowchart illustrating an example method of converting query structures for information retrieval from graph-based data structures using the semantic parsing system, according to various embodiments.

In FIG. 6, is a flowchart of operations of the semantic parsing system 150 in performing a method 600 of converting query structures for information retrieval from graph-based data structures, according to some example embodiments. Operations of the method 600 may be performed by the semantic parsing system 150, using components described herein.

Figure 7:
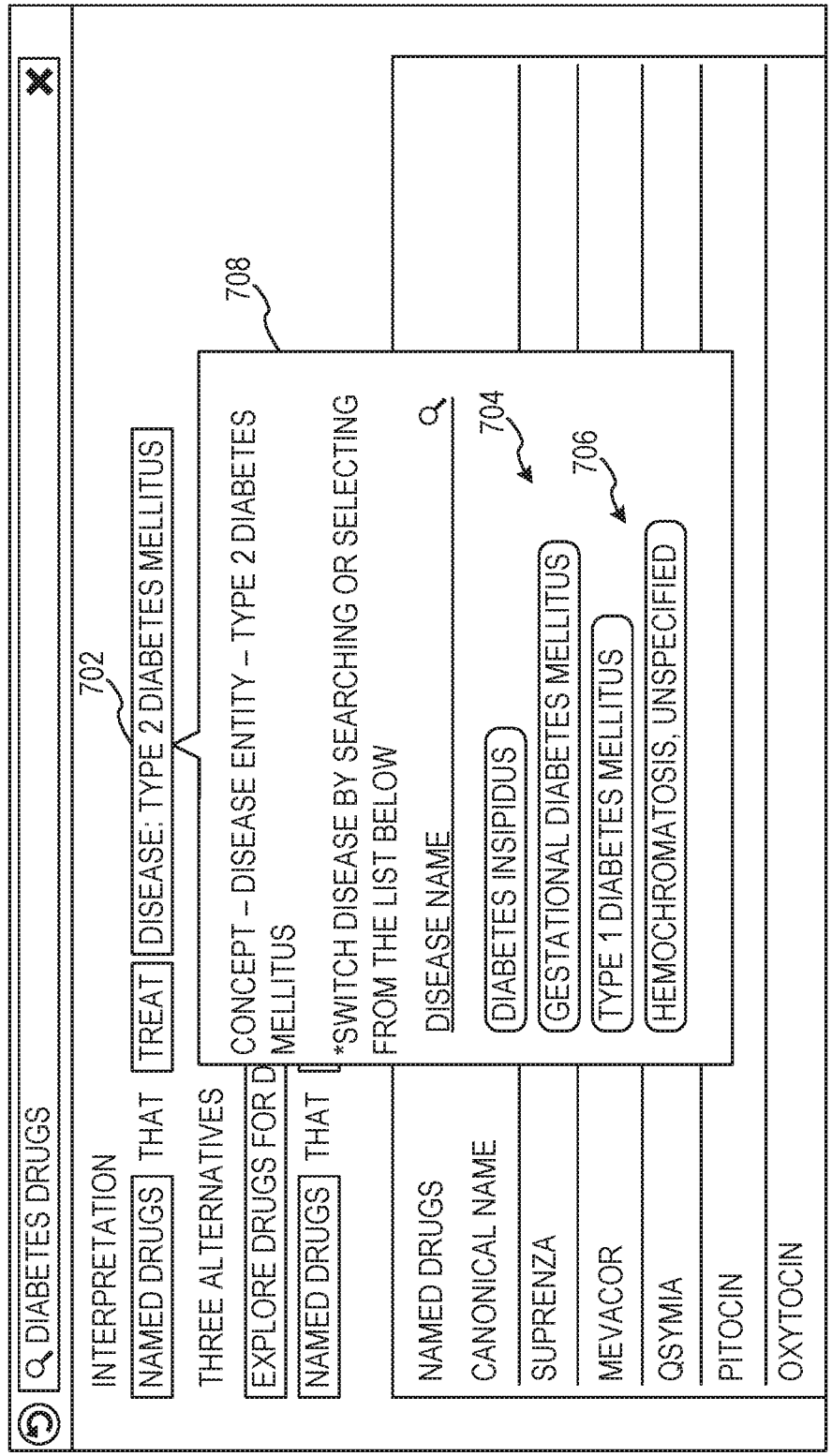
FIG. 7 is an example graphical user interface of the semantic parsing system, according to various embodiments

In operation 610, the modeling component 240 identifies an entity within a graph query element included in the graph query. As shown in FIG. 7, the entity 702 may be identified as a term, an item, an affliction, or any other searchable aspect of a database. The entity may be identified during transformation of the natural language query to the graph query, described above with respect to FIGS. 3-5.

In operation 620, the modeling component 240 determines one or more graph query elements related to the entity. The one or more graph query elements 704 may be identified in a manner similar to or the same as described above with respect to translating the natural language query to the graph query in FIG. 3 and the method 300.

In operation 630, the presentation component 250 generates one or more interface elements 706 related to the entity. In some embodiments, the interface elements 706 represent the one or more graph query elements. Each interface element may represent a distinct graph query element, such that if a plurality of graph query elements are identified a plurality of interface elements 706 are generated.

In operation 640, the modeling component 240 detects interaction with the graph query element associated with the entity. The modeling component 240 may detect interaction with the graph query element 702 via a tap, touch, mouse click, or any other suitable user interaction discernable within a graphical user interface presented on a computing device.

In operation 650, the presentation component 250 causes presentation of the one or more interface elements for the one or more graph query elements relating to the entity. In some embodiments, as shown in FIG. 7, the one or more graph query elements 704 or the interface elements 706 may be presented in a menu 708. The menu 708 may be a hovering menu, a drop down menu, a pop up window, or any other suitable selectable interface element or window. The menu 708 may present additional search operations or options mirroring those described above with respect to the graphical user interface 400 of FIG. 4.

In operation 660, the presentation component 250 cooperates with the modeling component 240 to replace the entity with a graph query element associated with the selected interface element within the graph query. In some embodiments, the entity is replaced by the selected interface element and corresponding graph query element upon detecting selection of an interface element of the one or more interface elements.

Semantic parsers, such as the semantic parsing system 150, are commonly evaluated using datasets in which texts are paired with their desired logical forms or denotations. Such evaluations may be effective but costly in terms of human labor. Embodiments of the present semantic parsing system 150 may be evaluated via increased usability.

Embodiments and aspects of the present disclosure were evaluated using pairs of tasks, classified into increasing levels of difficulty as measured by the number of terms they contained and the intricacy of the semantic operations required. For each participant involved in the evaluation, one of each pair was randomly assigned as a parser task and one as a Cypher task, for a total of ten tasks. Random assignment was used to even out any variable difficulty not accounted for by classifications used in example embodiments of the semantic parsing system 150. The tasks took the form of short summaries like "Objects to return: providers; Restriction: specialty is cardiac surgery." Clues contained in these summaries regarding how to formulate queries may be equally useful for English and Cypher query formulations or translations. Performance of embodiments of the semantic parsing system 150 were evaluated on the Cypher and English parts within subjects. These clues may not favor any one system. Similarly, within-subject comparisons may abstract away from participants' varying levels of expertise with Cypher graph queries.

Embodiments of the semantic parsing system were evaluated in the above-described manner by individuals having Cypher experience. The results of the study favored embodiments presented in the present disclosure. In the evaluation, the total time taken for the Cypher tasks was much lower using embodiments of the semantic parsing system 150 than for other search or parsing systems. The disclosed semantic parsing system 150 is flexible, powerful, and easy to deploy on new, large health knowledge graphs because the central aspects of the system are defined by the graph itself. The system is under active development; we aim to provide increasingly rich access to public health data. Embodiments of the semantic parsing system 150 improve usability of knowledge graph searching over graph query languages and are easier for novice users to navigate. Further, embodiments of the semantic parsing system 150 are easier to scale than pure natural language query systems. The semantic parsing system 150 enables expansion and scaling across a broad range of dataset and database domains with minimal or no human intervention or annotation.

Modules, Components, and Logic

Certain embodiments are described herein as including logic or a number of components, modules, or mechanisms. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

In some embodiments, a hardware component may be implemented mechanically, electronically, or any suitable combination thereof. For example, a hardware component may include dedicated circuitry or logic that is permanently configured to perform certain operations. For example, a hardware component may be a special-purpose processor, such as a Field-Programmable Gate Array (FPGA) or an Application Specific Integrated Circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations.

Accordingly, the phrase "hardware component" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented component" refers to a hardware component. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors.

Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API).

The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

Machine and Software Architecture

The components, methods, applications and so forth described in conjunction with FIGS. 2-6 are implemented in some embodiments in the context of a machine and an associated software architecture. In various embodiments, the components, methods, applications and so forth described above are implemented in the context of a plurality of machines, distributed across and communicating via a network, and one or more associated software architectures. The sections below describe representative software architecture(s) and machine (e.g., hardware) architecture that are suitable for use with the disclosed embodiments.

Software architectures are used in conjunction with hardware architectures to create devices and machines tailored to particular purposes. For example, a particular hardware architecture coupled with a particular software architecture will create a mobile device, such as a mobile phone, tablet device, or so forth. A slightly different hardware and software architecture may yield a smart device for use in the "internet of things," while yet another combination produces a server computer for use within a cloud computing architecture. Not all combinations of such software and hardware architectures are presented here as those of skill in the art can readily understand how to implement the present embodiments in different contexts from the disclosure contained herein.

Software Architecture

Figure 8:
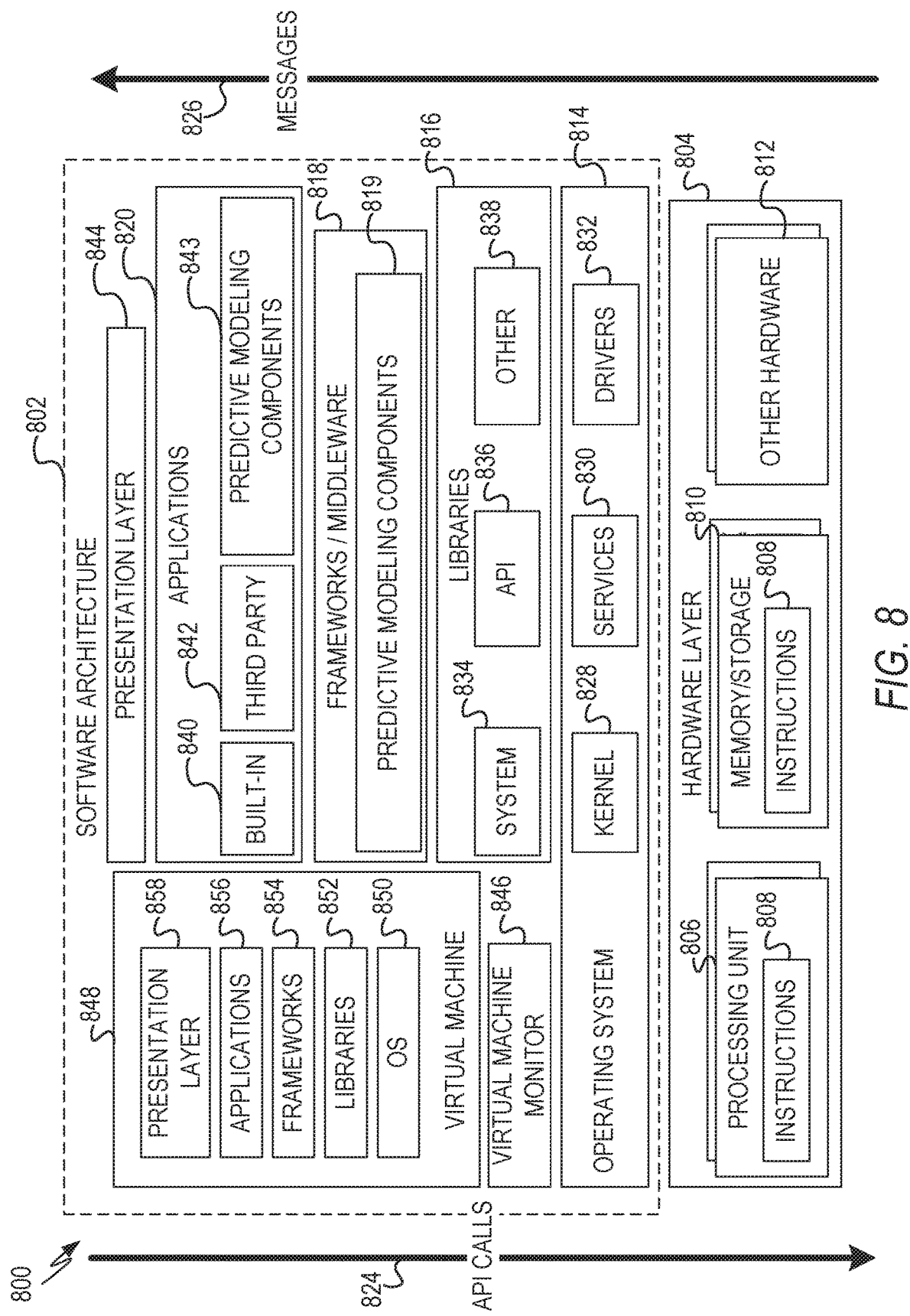
FIG. 8 is a block diagram illustrating an example of a software architecture that may be installed on a machine, according to some example embodiments.

FIG. 8 is a block diagram 800 illustrating a representative software architecture 802, which may be used in conjunction with various hardware architectures herein described. FIG. 8 is merely a non-limiting example of a software architecture and it will be appreciated that many other architectures may be implemented to facilitate the functionality described herein. The software architecture 802 may be executing on hardware such as machine 900 of FIG. 9 that includes, among other things, processors 910, memory 930, and Input/Output (I/O) components 950. A representative hardware layer 804 is illustrated and can represent, for example, the machine 800 of FIG. 8. The representative hardware layer 804 comprises one or more processing units 806 having associated executable instructions 808. Executable instructions 808 represent the executable instructions of the software architecture 802, including implementation of the methods, components, and so forth of FIGS. 2-7. Hardware layer 804 also includes memory and/or storage components 810, which also have executable instructions 808. Hardware layer 804 may also comprise other hardware as indicated by 812, which represents any other hardware of the hardware layer 804, such as the other hardware illustrated as part of machine 900.

In the example architecture of FIG. 8, the software 802 may be conceptualized as a stack of layers where each layer provides particular functionality. For example, the software 802 may include layers such as an operating system 814, libraries 816, frameworks/middleware 818, applications 820, and presentation layer 822. Operationally, the applications 820 and/or other components within the layers may invoke API calls 824 through the software stack and receive a response, returned values, and so forth, illustrated as messages 826 in response to the API calls 824. The layers illustrated are representative in nature and not all software architectures have all layers. For example, some mobile or special purpose operating systems may not provide a frameworks/middleware layer 818, while others may provide such a layer. Other software architectures may include additional or different layers.

The operating system 814 may manage hardware resources and provide common services. The operating system 814 may include, for example, a kernel 828, services 830, and drivers 832. The kernel 828 may act as an abstraction layer between the hardware and the other software layers. For example, the kernel 828 may be responsible for memory management, processor management (e.g., scheduling), component management, networking, security settings, and so on. The services 830 may provide other common services for the other software layers. The drivers 832 may be responsible for controlling or interfacing with the underlying hardware. For instance, the drivers 832 may include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 816 may provide a common infrastructure that may be utilized by the applications 820 and/or other components and/or layers. The libraries 816 typically provide functionality that allows other software components to perform tasks in an easier fashion than to interface directly with the underlying operating system 814 functionality (e.g., kernel 828, services 830 and/or drivers 832). The libraries 816 may include system 834 libraries (e.g., C standard library) that may provide functions such as memory allocation functions, string manipulation functions, mathematic functions, and the like. In addition, the libraries 816 may include API libraries 836 such as media libraries (e.g., libraries to support presentation and manipulation of various media format such as Moving Pictures Experts Group 4 (MPEG4), H.264, MP3, Advanced Audio Coding (AAC), Adaptive Multi-Rate (AMR), Joint Photographic Experts Group (JPEG), Portable Network Graphics (PNG)), graphics libraries (e.g., an OpenGL framework that may be used to render two dimensions and three dimensions in a graphic content on a display), database libraries (e.g., SQLite that may provide various relational database functions), web libraries (e.g., WebKit that may provide web browsing functionality), and the like. The libraries 816 may also include a wide variety of other libraries 838 to provide many other APIs to the applications 820 and other software components/modules.

The frameworks 818 (also sometimes referred to as middleware) may provide a higher-level common infrastructure that may be utilized by the applications 820 and/or other software components/modules. For example, the frameworks 818 may provide various graphical user interface functions, high-level resource management, high-level location services, and so forth. The frameworks 818 may provide a broad spectrum of other APIs that may be utilized by the applications 820 and/or other software components/modules, some of which may be specific to a particular operating system or platform. In some example embodiments, predictive modeling components 819 (e.g., one or more components of the semantic parsing systems 150) may be implemented at least in part within the middleware/frameworks 818. For example, in some instances, at least a portion of the database component 220 and the presentation component 250, providing graphical and non-graphical user interface functions, may be implemented in the middleware/frameworks 818. Similarly, in some example embodiments, portions of one or more of the receiver component 210, the database component 220, the semantic parsing component 230, the modeling component 240, and the presentation component 250 may be implemented in the middleware/frameworks 818.

The applications 820 include built-in applications 840, third party applications 842, and/or predictive modeling components 843 (e.g., user facing portions of one or more of the components of the predictive modeling system 150). Examples of representative built-in applications 840 may include, but are not limited to, a contacts application, a browser application, a book reader application, a location application, a media application, a messaging application, and/or a game application. Third party applications 842 may include any of the built-in applications as well as a broad assortment of other applications. In a specific example, the third-party application 842 (e.g., an application developed using the Android™ or iOS™ software development kit (SDK) by an entity other than the vendor of the particular platform) may be mobile software running on a mobile operating system such as iOS™, Android™, Windows® Phone, or other mobile operating systems. In this example, the third-party application 842 may invoke the API calls 824 provided by the mobile operating system such as operating system 814 to facilitate functionality described herein. In various example embodiments, the user facing portions of the predictive modeling components 843 may include one or more components or portions of components described with respect to FIG. 2. For example, in some instances, portions of the receiver component 210, the database component 220, the semantic parsing component 230, the modeling component 240, and the presentation component 250, associated with user interface elements (e.g., data entry and data output functions), may be implemented in the form of an application.

The applications 820 may utilize built in operating system functions (e.g., kernel 828, services 830 and/or drivers 832), libraries (e.g., system 834, APIs 836, and other libraries 838), frameworks/middleware 818 to create user interfaces to interact with users of the system. Alternatively, or additionally, in some systems interactions with a user may occur through a presentation layer, such as presentation layer 844. In these systems, the application/component "logic" can be separated from the aspects of the application/component that interact with a user.

Some software architectures utilize virtual machines. In the example of FIG. 8, this is illustrated by virtual machine 848. A virtual machine creates a software environment where applications/components can execute as if they were executing on a hardware machine (such as the machine of FIG. 9, for example). A virtual machine is hosted by a host operating system (operating system 814 in FIG. 8) and typically, although not always, has a virtual machine monitor 846, which manages the operation of the virtual machine as well as the interface with the host operating system (i.e., operating system 814). A software architecture executes within the virtual machine such as an operating system 850, libraries 852, frameworks/middleware 854, applications 856 and/or presentation layer 858. These layers of software architecture executing within the virtual machine 848 can be the same as corresponding layers previously described or may be different.

Example Machine Architecture and Machine-Readable Medium

Figure 9:
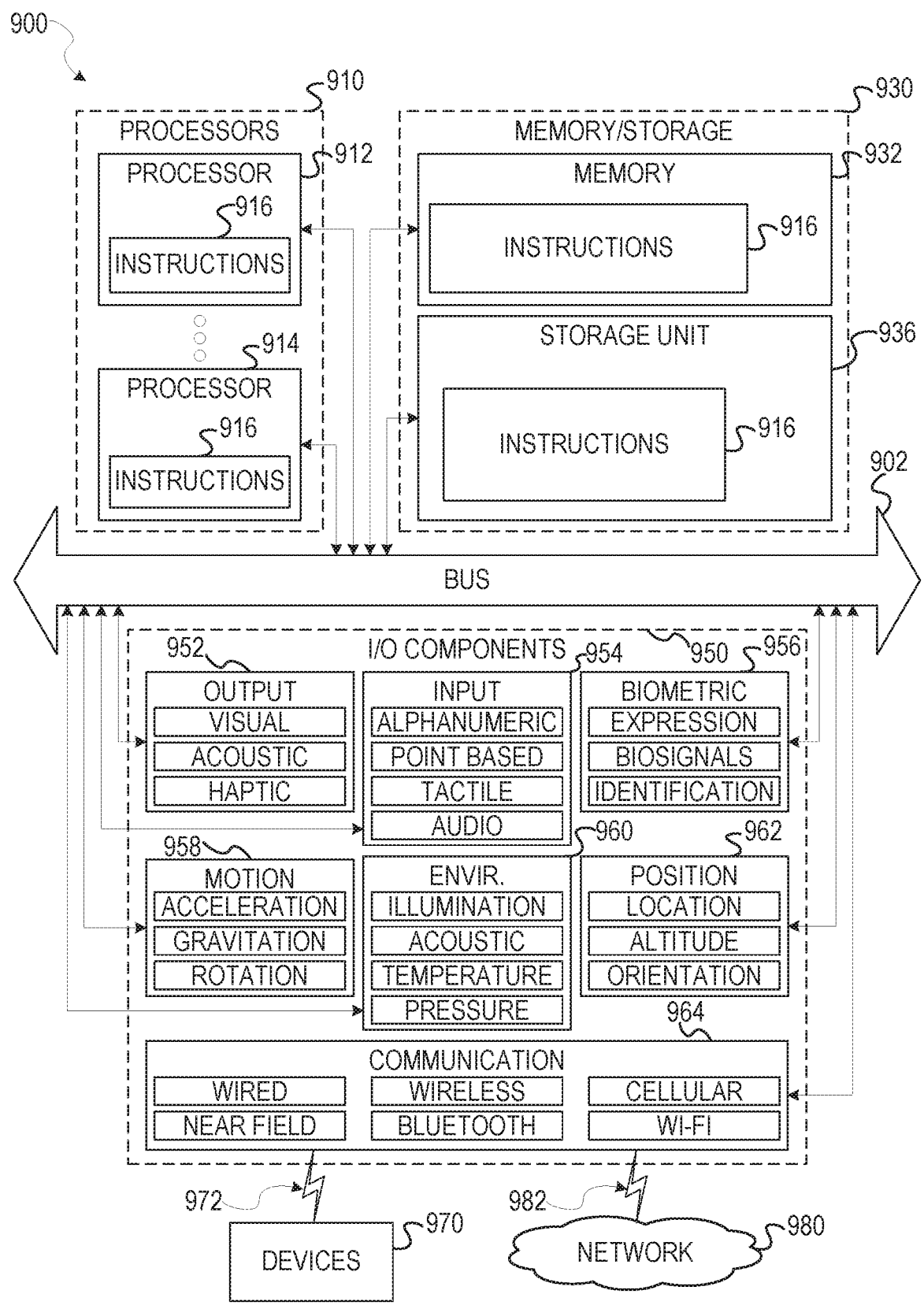
FIG. 9 illustrates a diagrammatic representation of a machine in the form of a computer system within which a set of instructions may be executed for causing the machine to perform any one or more of the methodologies discussed herein, according to an example embodiment.

FIG. 9 is a block diagram illustrating components of a machine 900, according to some example embodiments, able to read instructions (e.g., processor executable instructions) from a machine-readable medium (e.g., a non-transitory machine-readable storage medium) and perform any one or more of the methodologies discussed herein. Specifically, FIG. 9 shows a diagrammatic representation of the machine 900 in the example form of a computer system, within which instructions 916 (e.g., software, a program, an application, an applet, an app, or other executable code) for causing the machine 900 to perform any one or more of the methodologies discussed herein may be executed. For example, the instructions may cause the machine to execute methods described herein. Additionally, or alternatively, the instructions may implement the receiver component 210, the database component 220, the semantic parsing component 230, the modeling component 240, and the presentation component 250 of FIG. 2, and so forth. The instructions transform the general, non-programmed machine into a particular machine programmed to carry out the described and illustrated functions in the manner described.

In alternative embodiments, the machine 900 operates as a standalone device or may be coupled (e.g., networked) to other machines in a networked system. In a networked deployment, the machine 900 may operate in the capacity of a server machine or a client machine in a server-client network environment, or as a peer machine in a peer-to-peer (or distributed) network environment. The machine 900 may comprise, but not be limited to, a server computer, a client computer, a personal computer (PC), a tablet computer, a laptop computer, a netbook, a set-top box, an entertainment media system, a web appliance, a network router, a network switch, a network bridge, or any machine capable of executing the instructions 916, sequentially or otherwise, that specify actions to be taken by machine 900. In some example embodiments, in the networked deployment, one or more machines may implement at least a portion of the components described above. The one or more machines interacting with the machine 900 may comprise, but not be limited to a PDA, an entertainment media system, a cellular telephone, a smart phone, a mobile device, a wearable device (e.g., a smart watch), a smart home device (e.g., a smart appliance), and other smart devices. Further, while only a single machine 900 is illustrated, the term "machine" shall also be taken to include a collection of machines 900 that individually or jointly execute the instructions 916 to perform any one or more of the methodologies discussed herein.

The machine 900 may include processors 910, memory 930, and I/O components 950, which may be configured to communicate with each other such as via a bus 902. In an example embodiment, the processors 910 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), anASIC, a Radio-Frequency Integrated Circuit (RFIC), another processor, or any suitable combination thereof) may include, for example, processor 912 and processor 914 that may execute instructions 916. The term "processor" is intended to include multi-core processor that may comprise two or more independent processors (sometimes referred to as "cores") that may execute instructions contemporaneously. Although FIG. 9 shows multiple processors, the machine 900 may include a single processor with a single core, a single processor with multiple cores (e.g., a multi-core process), multiple processors with a single core, multiple processors with multiples cores, or any combination thereof.

The memory/storage 930 may include a memory 932, such as a main memory, or other memory storage, and a storage unit 936, both accessible to the processors 910 such as via the bus 902. The storage unit 936 and memory 932 store the instructions 916 embodying any one or more of the methodologies or functions described herein. The instructions 916 may also reside, completely or partially, within the memory 932, within the storage unit 936, within at least one of the processors 910 (e.g., within the processor's cache memory), or any suitable combination thereof, during execution thereof by the machine 900. Accordingly, the memory 932, the storage unit 936, and the memory of processors 910 are examples of machine-readable media.

As used herein, "machine-readable medium" means a device able to store instructions and data temporarily or permanently and may include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 916. The term "machine-readable medium" shall also be taken to include any medium, or combination of multiple media, that is capable of storing instructions (e.g., instructions 916) for execution by a machine (e.g., machine 900), such that the instructions, when executed by one or more processors of the machine 900 (e.g., processors 910), cause the machine 900 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 950 may include a wide variety of components to receive input, provide output, produce output, transmit information, exchange information, capture measurements, and so on. The specific I/O components 950 that are included in a particular machine will depend on the type of machine. For example, portable machines such as mobile phones will likely include a touch input device or other such input mechanisms, while a headless server machine will likely not include such a touch input device. It will be appreciated that the I/O components 950 may include many other components that are not shown in FIG. 9. The I/O components 950 are grouped according to functionality merely for simplifying the following discussion and the grouping is in no way limiting. In various example embodiments, the I/O components 950 may include output components 952 and input components 954. The output components 952 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 954 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 950 may include biometric components 956, motion components 957, environmental components 960, or position components 962 among a wide array of other components. For example, the biometric components 956 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 958 may include acceleration sensor components (e.g., accelerometer), gravitation sensor components, rotation sensor components (e.g., gyroscope), and so forth. The environmental components 960 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detect sensors to detection concentrations of hazardous gases for safety or to measure pollutants in the atmosphere), or other components that may provide indications, measurements, or signals corresponding to a surrounding physical environment. The position components 962 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 950 may include communication components 964 operable to couple the machine 900 to a network 980 or devices 970 via coupling 982 and coupling 972, respectively. For example, the communication components 964 may include a network interface component or other suitable device to interface with the network 980. In further examples, communication components 964 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 970 may be another machine or any of a wide variety of peripheral devices (e.g., a peripheral device coupled via a USB).

Moreover, the communication components 964 may detect identifiers or include components operable to detect identifiers. For example, the communication components 964 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 964, such as, location via Internet Protocol (IP) geo-location, location via Wi-Fi® signal triangulation, location via detecting a NFC beacon signal that may indicate a particular location, and so forth.

Transmission Medium

In various example embodiments, one or more portions of the network 980 may be an ad hoc network, an intranet, an extranet, a VPN, a LAN, a WLAN, a WAN, a WWAN, a MAN, the Internet, a portion of the Internet, a portion of the PSTN, a plain old telephone service (POTS) network, a cellular telephone network, a wireless network, a Wi-Fi® network, another type of network, or a combination of two or more such networks. For example, the network 980 or a portion of the network 980 may include a wireless or cellular network and the coupling 982 may be a Code Division Multiple Access (CDMA) connection, a Global System for Mobile communications (GSM) connection, or other type of cellular or wireless coupling. In this example, the coupling 982 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The instructions 916 may be transmitted or received over the network 980 using a transmission medium via a network interface device (e.g., a network interface component included in the communication components 964) and utilizing any one of a number of well-known transfer protocols (e.g., hypertext transfer protocol (HTTP)). Similarly, the instructions 916 may be transmitted or received using a transmission medium via the coupling 972 (e.g., a peer-to-peer coupling) to devices 970. The term "transmission medium" shall be taken to include any intangible medium that is capable of storing, encoding, or carrying instructions 916 for execution by the machine 900, and includes digital or analog communications signals or other intangible medium to facilitate communication of such software.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, components, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is claimed is:

1. A method of graph-backed processing of a natural language query to search a graph database, wherein the graph database comprises nodes and edges having associated attributes, and the graph database is organized as a plurality of sub-graphs each corresponding to a respective knowledge domain from a respective data source, the plurality of sub-graphs are connected via a canonical layer, with edges connecting the sub-graphs with attributes indicative of relationships between nodes of sub-graphs of the plurality of sub-graphs that are based on related attributes of the nodes such that the graph database has a schema indicative of entities, concepts, and relations, the method comprising:
  receiving, at one or more hardware processors of a machine, a natural language query including a set of terms;
  generating, by the one or more hardware processors, a graph query including graph terms corresponding to the set of terms of the natural language query, the generating the graph query comprising:
    parsing the natural language query to identify terms and relationships between the terms, using the schema of the graph database, wherein at least a portion of the identified terms correspond to attributes of nodes in the graph database and at least a portion of the relationships correspond to attributes of edges connecting the plurality of sub-graphs in the graph database;
  searching one or more sub-graphs of the plurality of sub-graphs of the graph database using the graph query; and
  returning a set of results based on the searching.

2. The method of claim 1, further comprising generating the canonical layer by using a machine learning technique to generate a model to incorporate the nodes and edges into the canonical layer.

3. The method of claim 1, wherein parsing the natural language query comprises using a grammar rule, a syntax rule, a lexicon, and/or a language model defined by the graph database.

4. The method of claim 3, wherein the grammar rule is generated at least in part using the graph schema of the graph database.

5. The method of claim 3, wherein:
  generating the graph query comprises performing an entity detection operation using the language model; and
  the language model is trained on name-type attributes of nodes in the graph database.

6. The method of claim 5, wherein:
  generating the graph query comprises performing a lookup operation to generate the graph query using an entity index for the graph database.

7. The method of claim 6, further comprising automatically generating the entity index from the graph database.

8. The method of claim 3, wherein the lexicon is generated from nodes and edges of the graph database.

9. A method of graph-backed processing of a natural language query to search a graph database comprising nodes and edges, with the nodes and edges each comprising attributes such that the graph database has a schema indicative of entities, concepts, and relations, the method comprising:
  receiving, at one or more hardware processors of a machine, a natural language query including a set of terms;
  generating, by the one or more hardware processors, a graph query including graph terms corresponding to the set of terms of the natural language query, the generating the graph query comprising parsing the natural language query to identify terms and relationships between the terms, using the schema of the graph database;
  searching the graph database using the graph query to generate a set of results based on the searching;
  rendering on a user interface search results of the set of results and a representation of the natural language query with selectable user interface elements representing elements of the graph query;
  in response to user input selecting a selectable graphical user interface element, generating, using the graph database, one or more alternative search terms related to one or more graph terms in the graph query; and
  in response to user input selecting an alternative search term of the one or more alternative search terms, generating alternative search results based on replacing a graph term in the graph query with the selected alternative search term of the one or more alternative search terms.

10. The method of claim 9, further comprising:
generating the schema based on a canonical layer connecting a plurality of sub-graphs of the graph database, each of the plurality of sub-graphs corresponding to a respective knowledge domain, the canonical layer comprising edges with attributes indicative of relationships between nodes of sub-graphs of the plurality of sub-graphs that are based on related attributes of the nodes.

11. The method of claim 9, further comprising:
generating a representation of the graph query by:
  segmenting the graph query into a first set of graph query elements corresponding to the set of terms in the natural language query; and
  inferring from the natural language query to determine a second set of graph query elements;
displaying the representation of the graph query, wherein the representation of the graph query comprises the first set of graph query elements and the second set of graph query elements; and
receiving user interaction indicative of a replacement of one or more graph terms.

12. The method of claim 11, wherein:
one or more of the first set of graph query elements represent or interpret at least a portion of the natural language query; and
the second set of graph query elements comprise a set of connective terms linking the set of graph query elements as an approximation of the natural language query.

13. A system comprising:
one or more hardware processors;
a graph database comprising:
  a plurality of sub-graphs each representing a respective dataset associated with a respective knowledge domain; and
  a canonical layer connecting the plurality of sub-graphs, wherein the canonical layer comprises nodes and edges, wherein the edges are indicative of relationships among the plurality of sub-graphs, wherein the relationships are based in part on related attributes of individual nodes within the plurality of sub-graphs; and a non-transitory processor-readable storage medium coupled to the one or more hardware processors, the processor-readable storage medium storing processor-executable instructions that, when executed by the one or more processors, cause the one or more processors to:

receive a natural language query including a set of terms;

parse the natural language query using the relationships indicated by the canonical layer of the graph database to generate a graph query, wherein the graph query includes graph terms corresponding to the set of terms of the natural language query;

search one or more sub-graphs of the plurality of sub-graphs using the graph query; and return a set of results based on the search.

14. The system of claim 13, wherein the instructions for parsing the natural language query further comprise instructions configured to parse the natural language query using one or more of a grammar rule, a syntax rule, a lexicon, and/or a language model to generate the graph terms in the graph query, wherein the grammar rule, the syntax rule, the lexicon, and/or the language model are defined by the graph database.

15. The system of claim 14, wherein the grammar rule is generated at least in part using a graph schema of the graph database.

16. The system of claim 14, wherein the instructions for generating the graph query further comprise instructions configured to perform an entity detection operation using the language model, wherein the language model is trained on name-type attributes of nodes in the graph database.

17. The system of claim 14, wherein the lexicon is generated from nodes and edges of the graph database.

18. The system of claim 12, wherein the instructions for generating the graph query further comprise instructions for performing a look-up operation to generate the graph query using an entity index for the graph database.

19. A non-transitory processor-readable storage medium comprising instructions that, when executed by one or more processors of a device, cause the device to implement operations for graph-backed processing of a natural language query to search a graph database, wherein the graph database comprises a plurality of sub-graphs and a canonical layer indicating relationships between related nodes of the sub-graphs, each sub-graph being associated with a respective knowledge domain and comprising nodes, the operations comprising:

receiving a natural language query including a set of terms;

parsing, using at least the relationships indicated in the canonical layer, the natural language query to generate a graph query including graph terms corresponding to the set of terms of the natural language query, wherein the graph database comprises a plurality of sub-graphs each associated with a respective knowledge domain;

searching one or more sub-graphs of the plurality of sub-graphs using the graph query;

returning a set of results based on the search; and automatically updating the canonical layer of the graph database by using a machine learning model to incorporate new relationships between related nodes of the sub-graphs, whereby the searching automatically adapts.

20. The storage medium of claim 19, wherein the canonical layer comprises one or more edges generated based on related attributes of individual nodes within the connected sub-graphs.

21. The storage medium of claim 19, wherein the instructions for parsing the set of terms of the natural language query further comprise instructions configured to:

generate one or more of a language model, a lexicon, and/or a grammar or syntax rule using the graph database; and parse the set of terms of the natural language query to generate the graph query using the one or more of the language model, the lexicon, and/or the grammar or syntax rule.

22. The storage medium of claim 21, wherein the grammar or syntax rule is generated at least in part using a graph schema of the graph database.

23. The storage medium of claim 21, wherein the instructions for generating the graph query further comprises instructions configured to perform an entity detection operation using the language model, wherein the language model is trained on name-type attributes of nodes in the graph database.

24. The storage medium of claim 21, wherein the lexicon is generated from nodes and edges of the graph database.

25. The storage medium of claim 19, wherein the instructions for generating the graph query further comprises instructions configured to perform a look-up operation to generate the graph query using an entity index for the graph database.

26. The storage medium of claim 25, further comprising instructions configured to automatically generate the entity index from the graph database.

* * * * *